(12) United States Patent
Grass et al.

(10) Patent No.: US 7,786,201 B2
(45) Date of Patent: Aug. 31, 2010

(54) MIXTURE OF DIISONONYL ESTERS OF 1,2-CYCLOHEXANEDICARBOXYLIC ACID, METHOD FOR THE PRODUCTION THEREOF AND USE OF THESE MIXTURES

(75) Inventors: Michael Grass, Haltern am See (DE); Arne Lang, Marl (DE)

(73) Assignee: Evonik Oxeno GmbH, Marl (DE)

( * ) Notice: Subject to any disclaimer, the term of this patent is extended or adjusted under 35 U.S.C. 154(b) by 315 days.

(21) Appl. No.: 11/911,691

(22) PCT Filed: Apr. 27, 2006

(86) PCT No.: PCT/EP2006/061889

§ 371 (c)(1), (2), (4) Date: Oct. 16, 2007

(87) PCT Pub. No.: WO2006/136471

PCT Pub. Date: Dec. 28, 2006

(65) Prior Publication Data

US 2008/0188601 A1 Aug. 7, 2008

(30) Foreign Application Priority Data

Jun. 22, 2005 (DE) .................. 10 2005 028 752

(51) Int. Cl.
*C08K 5/09* (2006.01)
*C07C 69/00* (2006.01)

(52) U.S. Cl. ...................... 524/321; 560/129

(58) Field of Classification Search .................. 524/321
See application file for complete search history.

(56) References Cited

U.S. PATENT DOCUMENTS 7,205,349 B2* 4/2007 Koch et al. .................. 524/284

| | | |
|---|---|---|
| 2003/0069135 A1 | 4/2003 | Kober et al. |
| 2004/0260113 A1 | 12/2004 | Bueschken et al. |
| 2005/0038285 A1 | 2/2005 | Maschmeyer et al. |
| 2005/0101800 A1 | 5/2005 | Bueschken et al. |
| 2006/0041167 A1* | 2/2006 | Grass et al. .................. 562/509 |
| 2006/0167151 A1 | 7/2006 | Grass et al. |
| 2006/0183936 A1 | 8/2006 | Grass et al. |
| 2007/0060768 A1 | 3/2007 | Grass et al. |

FOREIGN PATENT DOCUMENTS

| | | |
|---|---|---|
| DE | 103 21 100 | 12/2004 |
| EP | 1 314 772 | 5/2003 |
| EP | 1 475 071 | 11/2004 |
| WO | 2004/009526 | 1/2004 |
| WO | 2004/081127 | 9/2004 |

OTHER PUBLICATIONS

U.S. Appl. No. 11/739,345, filed Apr. 24, 2007, Grass, et al.
U.S. Appl. No. 10/575,100, filed Apr. 10, 2006, Grass, et al.
U.S. Appl. No. 11/622,567, filed Jan. 12, 2007, Grass.
U.S. Appl. No. 10/489,317, filed Aug. 11, 2004, Bueschken, et al.
U.S. Appl. No. 10/490,028, filed Oct. 4, 2004, Maschmeyer, et al.
U.S. Appl. No. 10/474,044, filed Oct. 15, 2003, Bueschken, et al.
U.S. Appl. No. 10/511,595, filed Nov. 2, 2004, Grass, et al.
U.S. Appl. No. 10/519,413, filed Jan. 6, 2005, Grass, et al.
U.S. Appl. No. 11/322,349, filed Jan. 3, 2006, Grass, et al.

* cited by examiner

*Primary Examiner*—Ling-Siu Choi
*Assistant Examiner*—Hui Chin
(74) *Attorney, Agent, or Firm*—Oblon, Spivak, McClelland, Maier & Neustadt, L.L.P.

(57) ABSTRACT

The present invention relates to a mixture of diisononyl esters of 1,2-cyclohexanedicarboxylic acid, wherein the isononyl radicals of the diisononyl esters present in the mixture have a degree of branching of from 1.2 to 2.0, to a process for its preparation and to the use of such mixtures.

24 Claims, No Drawings

MIXTURE OF DIISONONYL ESTERS OF 1,2-CYCLOHEXANEDICARBOXYLIC ACID, METHOD FOR THE PRODUCTION THEREOF AND USE OF THESE MIXTURES

The present invention relates to a mixture of diisononyl esters of 1,2-cyclohexanedicarboxylic acid. The present invention likewise relates to a process for preparing such mixtures and to their use.

Alicyclic polycarboxylic esters, for example the esters of cyclohexane-1,2-dicarboxylic acid, are used as a lubricant component and an assistant in metal processing. They also find use as plasticizers for plastics such as polyvinyl chloride (PVC), polyvinyl butyral (PVB) and polyolefins.

For the plasticization of PVC, predominantly esters of phthalic acid, for example dibutyl, dioctyl, dinonyl or didecyl esters, are used at present. Since these phthalates are frequently being designated as harmful to health in recent times, there has to be a concern that their use in plastics might be restricted. WO 03/029339 states that di-2-ethylhexyl phthalates (DEHP, often also known as DOP) and diisononyl phthalates (DINP) can be replaced for most applications by di-2-ethylhexyl 1,2-cyclohexyldicarboxylate (DEHCH) and diisononyl 1,2-cyclohexanedicarboxylate (DINCH), since the corresponding ring-hydrogenated esters have similar properties with regard to their plasticizing action expressed by the Shore hardness to the non-ring-hydrogenated esters with the same alcohol component. Alicyclic polycarboxylic esters might therefore be available as replacements, albeit with a somewhat different performance profile overall, to replace the phthalates.

In most cases, the most economically viable route to the preparation of alicyclic polycarboxylic esters is the ring hydrogenation of the corresponding aromatic polycarboxylic esters, for example of the abovementioned phthalates. Some processes for this purpose have already become known:

U.S. Pat. Nos. 5,286,898 and 5,319,129 describe a process with which dimethyl terephthalate can be hydrogenated to the corresponding dimethyl hexahydroterephthalate over supported Pd catalysts doped with Ni, Pt and/or Ru, at temperatures greater than or equal to 140° C. and a pressure between 50 and 170 bar.

In DE 28 23 165, aromatic carboxylic esters are hydrogenated over supported Ni, Ru, Rh and/or Pd catalysts to the corresponding alicyclic carboxylic esters at from 70 to 250° C. and from 30 to 200 bar. U.S. Pat. No. 3,027,398 discloses the hydrogenation of dimethyl terephthalate over supported Ru catalysts at from 110 to 140° C. and from 3.5 to 10.5 MPa.

WO 00/78704 discloses a process for hydrogenating benzenepolycarboxylic esters to the corresponding alicyclic compounds. Preference is given to using supported catalysts which comprise Ru alone or together with at least one metal of transition group I, VII or VIII of the periodic table and have from 5 to 50% of macropores.

DE 101 61 010 describes the preparation of cyclohexane-1,2-dicarboxylic esters starting from a diene/maleic anhydride mixture via a reaction sequence which includes a Diels-Alder reaction.

It is also possible to obtain the cyclohexanedicarboxylic esters by esterifying cyclohexanedicarboxylic acid or suitable derivatives with the corresponding alcohols.

Frequently, mixtures of isomeric esters are used in industry. Based on EP 1 042 273 or DE 101 16 812, however, there is the suspicion that there is no fundamental difference in the properties of the various diisononyl cyclohexanedicarboxylates claimed there, which are obtainable, for example, from various diisononyl phthalates (DINP) by ring hydrogenation. In particular, the hydrogenation products of the DINP types, whose alcohol chains may be obtained on the basis of n-butene or isobutene, were referred to as suitable.

One of the most important phthalates is di-2-ethylhexyl phthalate (DEHP). Owing to a possible risk to health which might possibly arise from the use of this plasticizer, there is a search for plasticizers which might be able to substitute for the phthalates, especially DEHP, in sensitive applications, for example medical articles, toys or in the food contact sector.

It is therefore an object of the present invention to provide a plasticizer which has performance properties which enable DEHP to be replaced in some, preferably in a maximum number of applications.

It has been found that, surprisingly, the performance properties of diisononyl cyclohexanedicarboxylate can be adjusted by selection of the composition of the alcohol components such that they are suitable for replacing DEHP with a minimum level of cost and inconvenience. It has been found that, surprisingly, mixtures of diisononyl esters of 1,2-cyclohexanedicarboxylic acid whose isononyl radicals have a degree of branching of from 1.2 to 2.0 are particularly suitable as a replacement of DEHP as a plasticizer for PVC.

The present invention therefore provides a mixture of diisononyl esters of 1,2-cyclohexanedicarboxylic acid, wherein the isononyl radicals of the diisononyl esters present in the mixture have a degree of branching of from 1.2 to 2.0.

The present invention likewise provides a process for preparing mixtures of diisononyl esters of 1,2-cyclohexanedicarboxylic acid, which comprises using a mixture of isomeric nonanols which has a degree of branching of from 1.2 to 2.0 in the preparation of the diisononyl esters.

The present invention also provides for the use of the inventive mixtures in paints or coatings, in adhesives or adhesive components, in sealants or as plasticizers in plastics or plastic components or as a solvent.

The inventive mixtures have the advantage that they have a low viscosity in plastisols. Moreover, the loss of mass after thermal aging is low.

The inventive mixtures of diisononyl cyclohexanedicarboxylates (DINCH) also have the advantage that they have similar or better values for the cold flexibilization capacity than DEHP and that they have a profile deviating only marginally from that of DEHP with regard to most processing properties, for example in dry blends (powder mixtures). In the case of replacement of DEHP by the inventive DINCH, the required adaptations can thus remain restricted to a minimum.

The invention will be described by way of example hereinbelow without any intention that the invention, whose scope of protection is evident from the claims and the entire description, be restricted thereto. The claims too belong to the disclosure content of the present invention. When areas or areas of preference are specified in the text which follows, all theoretically possible individual values and part-areas lying within these areas are also included in the disclosure content of the present invention without these having been mentioned explicitly for reasons of better clarity.

In the context of the present invention, unless explicitly stated otherwise, 1,2-cyclohexanedicarboxylic acid or its esters refers to cis- or trans-isomerically pure compounds or else mixtures of cis- and trans-isomers of these compounds.

The mixture of diisononyl esters of 1,2-cyclohexanedicarboxylic acid (DINCH) is notable in that the isononyl radicals of the diisononyl esters present in the mixture have a degree of branching of from 1.2 to 2.0, preferably from 1.2 to 1.9, preferentially from 1.3 to 1.8 and more preferably from 1.3 to 1.7. The isononyl radicals are those which are based on primary isononanols.

The branching can, when exclusively 1,2-cyclohexanedicarboxylic acid radicals unsubstituted on the ring are present as in the present invention, be determined by $^1$H NMR or $^{13}$C NMR methods. In the present invention, the degree of branching is determined preferably with the aid of $^1$H NMR spectroscopy on a solution of the diisononyl esters in deuterochloroform (CDCl$_3$). For the recording of the spectra, for example, 20 mg of substance are dissolved in 0.6 ml of CDCl$_3$ (containing 1% by mass of TMS) and charged into an NMR tube having a diameter of 5 mm. Both the substance to be analyzed and the CDCl$_3$ used may first be dried over molecular sieve in order to rule out distortions of the measurements by any water present. The method of determining the degree of branching is advantageous over other methods of characterizing alcohol radicals, as described, for example, in WO 03/029339, since contaminations with water have substantially no influence on the measurement results and their evaluation. In principle, it is possible with $^1$H NMR spectroscopy to determine the degrees of branching of the primary isononyl radicals irrespective of whether the acid radical is based on a phthalic acid or a 1,2-cyclohexanecarboxylic acid, provided that the acids have no substituents which contain a —O—CH$_2$— group or a methyl group. The NMR spectroscopy analyses may in principle be carried out with any customary NMR instrument. For the present NMR spectroscopy analysis, an Avance 500 instrument from Bruker was used. The spectra were recorded at a temperature of 300 K with a delay of d1=5 seconds, 32 scans, a pulse length of 9.7 µs and a sweep width of 10 000 Hz with a 5 mm BBO probehead (broad band observer). The resonance signals are recorded against the chemical shifts of tetramethylsilane (TMS=0 ppm) at an internal standard. Other commercial NMR instruments are used to obtain comparable results with the same operating parameters.

The resulting $^1$H NMR spectra of the mixtures of diisononyl esters of 1,2-cyclohexanedicarboxylic acid have resonance signals which are formed (substantially) by the signals of the hydrogen atoms of the methyl group(s) of the isononyl groups in the range from 0.5 ppm up to the minimum of the lowest valley in the range from 0.9 to 1.1 ppm. The signals in the region of the chemical shifts from 3.6 to 4.4 ppm can be attributed (substantially) to the hydrogen atoms of the methylene group which is adjacent to the oxygen of the alcohol or of the alcohol radical. The quantification is effected by determining the area under the particular resonance signals, i.e. the area enclosed by the signal from the baseline. Commercial NMR instruments have devices for integrating the signal area. In the present NMR spectroscopy analysis, the integration was carried out with the aid of the software "xwinnmr", Version 3.5. Subsequently, the integral value of the signals in the range from 0.5 ppm up to the minimum of the lowest valley in the range from 0.9 to 1.1 ppm is divided by the integral value of the signals in the range from 3.6 to 4.4 ppm to obtain an intensity ratio which reports the ratio of the number of hydrogen atoms which are present in a methyl group to the number of hydrogen atoms which are present in a methylene group adjacent to an oxygen. Since three hydrogen atoms are present per methyl group and two hydrogen atoms are present per methylene group adjacent to an oxygen, the intensities have to be divided by 3 and 2 respectively in order to obtain the ratio of the number of methyl groups in the isononyl radical to the number of methylene groups adjacent to an oxygen in the isononyl radical. Since a linear primary nonanol which has only one methyl group and one methylene group adjacent to an oxygen does not comprise any branching and accordingly has a degree of branching of 0, the quantity 1 then has to be subtracted from the ratio.

The degree of branching V can thus be calculated from the measured intensity ratio by the following formula I:

$$V = \tfrac{2}{3} * I(CH_3)/I(OCH_2) - 1$$

where V=degree of branching, I(CH$_3$)=area integral which is attributed substantially to the methyl hydrogen atoms and I(OCH$_2$)=area integral of the methylene hydrogen atoms adjacent to the oxygen.

Nonyl alcohols which are obtained by hydrolyzing the inventive diisononyl esters preferably have less than 10 mol %, preferentially less than 5 mol %, more preferably less than 1 mol % and most preferably from 0.5 to 0.0001 mol % of the 3,5,5-trimethylhexanol. The diisononyl esters can be hydrolyzed by customary methods by reaction with alkaline media (see, for example, Ullmann's Enzyklopädie der Technischen Chemie, 5 Ed. A 10, p. 254-260, 1986). The proportion of 3,5,5-trimethylhexanol can be determined in a customary manner by gas chromatography analysis methods (GC).

The inventive mixture can be obtained, for example, by hydrogenating diisononyl phthalates. The hydrogenation of the diisononyl phthalates can be carried out, for example, over a catalyst which comprises at least one metal from transition group VIII, especially from the triad of iron, cobalt, nickel, optionally together with at least one metal of transition group II, III, IV, V and/or VI of the periodic table. It is equally possible to carry out the hydrogenation of the diisononyl phthalates over ruthenium-containing catalysts. Such processes are described, for example, in EP 1042273, EP 1314714 and EP 0814098. The catalysts used may in particular be those which are based on a support which has a macropore fraction of less than 5%, for example Aerolyst 7711, Degussa AG. Such catalysts and the corresponding hydrogenation processes are described, for example, in DE 102 25 565 and DE 102 32 868, whose contents are explicitly incorporated by reference.

However, the inventive mixture may also be obtained by transesterifying esters of 1,2-cyclohexanedicarboxylic acid or by esterifying 1,2-cyclohexanedicarboxylic acid (or the corresponding anhydride) with a mixture of isomeric nonanols.

Particular preference is given to preparing the inventive mixture by the process according to the invention. This process for preparing mixtures of diisononyl esters of 1,2-cyclohexanedicarboxylic acid features the use of a mixture of isomeric nonanols which have a degree of branching of from 1.2 to 2.0 in the preparation of the diisononyl esters. In the process according to the invention, preference is given to using mixtures of isomeric nonanols which have relatively low branching, preferably having a degree of branching of from 1.2 to 1.9, preferentially a degree of branching of from 1.3 to 1.8 and more preferably from 1.3 to 1.7. The degree of branching specifies the number of branches in the molecule. 1-Nonanol has, for example, a degree of branching of 0; 3,5,5-trimethylhexanol has a degree of branching of 3. The degree of branching of the mixture arises from the sum of the degrees of branching of the individual components multiplied by the particular fraction of the individual component divided by the sum of the fractions of all individual components. In the simplest case, the degree of branching for mixtures can be determined by directly determining the fraction of the individual components. When such a determination is not possible, the degree of branching can be determined for mixtures of primary isomeric nonanols, for example, by means of $^1$H NMR analogously to the above-described method. Since, in a $^1$H NMR spectrum of a mixture of primary $C_9$ alcohols, the signals which are attributed substantially to the hydrogen atoms of the methylene group which is adjacent to the oxygen of the alcohol or of the alcohol radical occur in the range from 3.0 to 3.9 ppm, the integral values of the signals in the range from 0.5 ppm up to the minimum of the lowest valley in the range from 0.9 to 1.1 ppm and of the signals in the range from 3.0 to 3.9 ppm are determined. The degree of branching V can be calculated for an isomer mixture in turn according to the abovementioned formula I.

More preferably, the mixtures of isomeric nonanols used in the process according to the invention contain less than 10 mol %, preferably less than 5 mol %, preferentially less than 1 mol % and in particular from 0 to 0.5 mol %, preferably less than 0.1 mol %, in particular from 0.0001 to 0.1 mol % and more preferably less than 0.05 mol %, in particular from 0.01 to 0.05 mol % of 3,5,5-trimethylhexanol. The isomer distributions in the mixtures of the isomeric nonanols may be determined with the customary analytical methods familiar to those skilled in the art, such as NMR spectroscopy, GC or GC-MS.

The mixtures of isomeric nonanols used in the process according to the invention may generally be prepared by hydroformylation of octenes which can in turn be obtained in different ways. The raw materials used to prepare the octenes are generally technical $C_4$ streams which initially comprise all isomeric $C_4$ olefins in addition to the saturated butanes and, in some cases, impurities such as $C_3$- and $C_5$-olefins and acetylenic compounds. Oligomerization of this olefin mixture affords predominantly isomeric octene mixtures in addition to higher oligomers such as $C_{12}$- and $C_{16}$-olefin mixtures. These octene mixtures are hydroformylated to the corresponding aldehydes and subsequently hydrogenated to the alcohol. The composition, i.e. the isomer distribution of the technical nonanol mixtures, is dependent upon the starting material and upon the oligomerization and hydroformylation processes.

The octene mixtures used may, for example, also be those which are obtained via the so-called polygas process in which an oligomerization of $C_3/C_4$ mixtures is carried out over a solid acidic catalyst, preferably over a solid phosphoric acid catalyst (SPA process). This process is described, inter alia, in the documents U.S. Pat. Nos. 6,284,938, 6,080,903, 6,072,093, 6,025,533, 5,990,367, 5,895,830, 5,856,604, 5,847,252 and 5,081,086. The nonanols obtained by these processes generally also contain fractions of octanols and decanols, so that the mean chain length here can deviate from 9 carbon atoms. However, this has no effect on the determination of the degree of branching V by the abovementioned method.

Particularly preferred mixtures of isomeric nonanols usable in the process according to the invention are those which are obtainable by hydroformylation and subsequent or simultaneous hydrogenation of a mixture of isomeric octenes, the mixture of isomeric octenes being obtained by contacting a hydrocarbon mixture which comprises butenes and has a fraction of isobutene of preferably less than 20% by weight, preferentially less than 10% by weight, more preferably less than 5% by weight, even more preferably less than 3% by weight, especially preferably less than 1% by weight, preferably between 0.01 and 1% by weight and more preferably between 0.05 and 0.5% by weight, with an oligomerization catalyst, especially with a catalyst comprising nickel oxide. The preparation of isomeric octenes by oligomerizing substantially linear butenes over supported nickel catalysts is known, for example, as the OCTOL process which is described, for example, in EP 0 395 857 or EP 1 029 839. In variants to the OCTOL process, for example, catalysts comprising Ti or Zr are used. Such alternative variants and especially the catalysts are described, for example, in EP 1 171 413.

The mixtures of isomeric octenes are subsequently sent to a hydroformylation. The hydroformylation may be effected in the presence of modified or unmodified cobalt or rhodium catalysts. Preference is given to effecting the hydroformylation in the presence of unmodified cobalt compounds. The hydroformylation is typically followed subsequently by a hydrogenation. Such hydroformylation/hydrogenation processes are known, for example, from EP 0 850 905 and EP 1 172 349, to which reference is made here explicitly and whose content is incorporated in the disclosure content of the present patent. The hydroformylation may also be effected in the presence of rhodium catalysts. Such hydroformylation processes are common knowledge. Specific processes for hydroformylation, which are particularly suitable for preparing mixtures of isomeric nonanols usable in the process according to the invention, are described, for example, in WO 2004/020380 or DE 103 27 435, to which reference is made here explicitly and whose contents are incorporated in the disclosure content of the present patent. The processes described there are carried out in the presence of cyclic carbonic esters.

It may also be advantageous first to fractionate the mixture of isomeric octenes as described in EP 1 172 349 before it is fed to the hydroformylation. In this way, it is possible to obtain octene fractions which are particularly suitable for preparing mixtures of isomeric nonanols usable in the process according to the invention. From the fractions, it is then possible in a relatively simple manner, by mixing suitable fractions, to obtain a mixture of isomeric octenes which is suitable for preparing mixtures of isomeric nonanols for use in the process according to the invention.

However, the mixture of isomeric nonanols used in the process according to the invention may also be a mixture which is obtained by mixing isomerically pure nonanols and/or fractions of a plurality of isomeric nonanols. Numerous isomerically pure nonanols are commercially available. Likewise commercially available are nonanol mixtures or fractions which do not have the preferred properties for the process according to the invention. Simple mixing of such isomerically pure nonanols with nonanol mixtures makes it possible to prepare mixtures of nonanols which lead to esters with the desired properties in the esterification with cyclohexanedioc acid or its anhydride. In particular, it is possible by such simple mixing to obtain mixtures of nonanols which have the desired fraction of 3,5,5-trimethylhexanol and of other components.

In a preferred embodiment of the process according to the invention for preparing mixtures of diisononyl esters of 1,2-cyclohexanedicarboxylic acid, the mixture of isomeric nonanols which has a degree of branching of from 1.2 to 2.0, preferably a degree of branching of from 1.2 to 1.9, preferably from 1.3 to 1.8 and more preferably from 1.3 to 1.7 is first reacted with phthalic acid or phthalic anhydride in an esterification step to give diisononyl phthalates (DINP) and these diisononyl phthalates are subsequently hydrogenated.

The esterification can be effected in a known manner, for example by reacting phthalic acid or phthalic anhydride with a suitable mixture of isomeric nonanols. In principle, it is possible to use all known esterification processes as the esterification step in the process according to the invention. However, preference is given to effecting the esterification step by a process in which the water of reaction is removed by azeotropic distillation with the alcohol and the amount of liquid removed from the reaction by the azeotropic distillation is made up again fully or partly with the alcohol. The amount of liquid refers hereinbelow to the volume of liquid removed from the reaction by azeotropic distillation, consisting mainly of water of reaction and alcohol. Preference is given to full replacement of the amount of liquid removed.

This can be done, for example, by level-controlled feeding of alcohol into the reactor. For technical reasons, full replacement of the amount of liquid removed may be realizable only with difficulty, if at all. In these cases, the amount of liquid removed is replaced again only partly, for example only the alcohol but not the water of reaction removed, but in any case to an extent of more than 90%, preferably from 95 to 98%.

It may even be necessary to return more than the amount of liquid distilled off into the reactor, i.e., in addition to the amount of alcohol removed, the water of reaction is replaced and further alcohol is additionally added. In this embodiment of the esterification, from 110 to 100%, preferably from 105% to 100%, of the amount of liquid removed is replaced by alcohol.

This embodiment of the esterification has the advantage that, in comparison to known batchwise processes, the reaction rate is increased. This allows the cycle time to be shortened, as a result of which a higher space-time yield is achieved.

The esterification may be carried out with autocatalysis or catalysis. The esterification catalysts used may be Lewis or Brønsted acids or organometallic substances which do not necessarily have to act as an acid. Preferred esterification catalysts are alkoxides, carboxylate salts or chelate compounds of titanium or zirconium, in which case the catalyst molecule may contain one or more metal atoms. In particular, tetra(isopropyl) orthotitanate and tetra(butyl) orthotitanate are used.

The esterification is preferably carried out in a reaction vessel in which the reaction mixture can be mixed intensively with the aid of a stirrer or of a circulation pump. The reactants and the catalyst may be introduced simultaneously or successively into the reactor. When one feedstock is solid at the introduction temperature, it is appropriate to initially charge the liquid use component. Solid feedstocks may be fed in as powder, granules, crystals or melt. In order to shorten the batch time, it is advisable to begin with the heating during the introduction. The catalyst may be introduced in pure form or as a solution, preferably dissolved in one of the feedstocks, at the start or only after attainment of the reaction temperature. Carboxylic anhydrides frequently react with alcohols autocatalytically, i.e. without catalysis, to give the corresponding ester carboxylic acids (monoesters), for example phthalic anhydride to give the phthalic monoester. Therefore, a catalyst is frequently not required until after the first reaction step.

The alcohol to be converted, which serves as the azeotroping agent, can be used in stoichiometric excess. Preference is given to using an excess of from 5 to 50%, more preferably from 10 to 30%.

The catalyst concentration depends upon the type of the catalyst. In the case of the titanium compounds used with preference, it is from 0.005 to 1.0% by mass based on the reaction mixture, in particular from 0.01 to 0.3% by mass.

When titanium catalysts are used, the reaction temperatures are between 160° C. and 270° C. The optimal temperatures depend upon the feedstocks, reaction progress and the catalyst concentration. They can be determined readily for each individual case by experiments. Higher temperatures increase the reaction rates and promote side reactions, for example water elimination from alcohols or formation of colored by-products. For the removal of the water of reaction, it is necessary that the alcohol can be distilled out of the reaction mixture. The desired temperature or the desired temperature range can be established by virtue of the pressure in the reaction vessel. In the case of low-boiling alcohols, the reaction is therefore carried out at elevated pressure, and at reduced pressure in the case of higher-boiling alcohols. For example, in the reaction of phthalic anhydride with a mixture of isomeric nonanols, a temperature range of from 170 to 250° C. in the pressure range from 0.1 MPa to 1.0 kPa is employed.

The amount of liquid to be returned to the reaction may consist partly or fully of alcohol which is obtained by working up the azeotropic distillate. It is also possible to carry out the workup at a later time and to replace the amount of liquid removed fully or partly with fresh alcohol, i.e. alcohol available from a reservoir vessel. In other embodiments of the esterification, the liquid removed is worked up to the alcohol, preferably to the pure alcohol.

After the reaction has ended, the reaction mixture, which consists substantially of full ester (target product) and excess alcohol, comprises, in addition to the catalyst and/or its subsequent products, small amounts of ester carboxylic acid(s) and/or unconverted carboxylic acid. To work up these crude ester mixtures, the excess alcohol is removed, the acidic compounds are neutralized, the catalyst is destroyed and the solid by-products formed are removed. In the course of this, the majority of the alcohol is distilled off at standard pressure or under reduced pressure. The last traces of the alcohol can be removed, for example, by steam distillation, especially in the temperature range from 120 to 225° C. The alcohol can be removed, for example, as the first or as the last workup step.

The acidic substances, such as carboxylic acids, ester carboxylic acids or, where present, the acidic catalysts, can be neutralized by addition of basic compounds of the alkali metals and alkaline earth metals. These may used in the form of their carbonates, hydrogencarbonates or hydroxides. The neutralizing agent may be used in solid form or preferably as a solution, especially as an aqueous solution. The neutralization can be carried out immediately after the esterification reaction has ended or after the majority of the excess alcohol has been distilled off. Preference is given to neutralization with sodium hydroxide solution immediately after the esterification has ended at temperatures above 150° C. The water introduced with the alkali can then be distilled off together with alcohol.

Further details of suitable esterification processes which can be used as the esterification step in the process according to the invention can be taken, for example, from EP 1 186 593 and EP 1 300 388, to which reference is made explicitly and whose contents are incorporated in the disclosure content of the present patent.

may be particularly advantageous when the esterification is carried out as described in DE 10 2005 021 075.9, to which reference is made explicitly and whose contents are incorporated in the subject matter of the present description. In the process described there for preparing carboxylic esters by metal-catalyzed reaction of mono-, di- or polycarboxylic acids or their anhydrides with alcohol in the presence of an excess of alcohol, the excess alcohol being removed after the esterification, the crude ester thus obtained being neutralized by addition of base and subsequently filtered, and at least a portion of the excess alcohol being removed by at least one steam distillation, a) in a first step, preferably after the esterification reaction has ended, the alcohol content in the esterification mixture is reduced to a content of less than or equal to 5% by mass by distillation, b) a first amount of base is added to the crude ester obtained in step a), so that the base, calculated in base equivalents, is in a molar ratio of from 10:1 to 1:1 with the metal atom of the esterification catalyst used, c) the mixture obtained in b) is subjected to a steam distillation and a second amount of base which corresponds at least to the amount which is needed to neutralize residual acid is added to the mixture at the start and/or in the course of the steam distillation.

In this embodiment of the process according to the invention, the hydrogenation of the diisononyl phthalates can be carried out, for example, over a catalyst which comprises at least one metal of transition group VIII, especially at least one metal from the triad of iron, cobalt, nickel, optionally together with at least one metal of transition group II, III, IV, V and/or VI of the periodic table. Preferred metals of transition group II, III, IV, V and/or VI are zinc and/or chromium. It is possible with very particular preference to carry out the hydrogenation of the diisononyl phthalates over ruthenium-containing catalysts. Such catalysts are described, for example, in EP 1042273, EP 1314714 and EP 0814098, to which reference is made explicitly. However, the catalysts used are preferably those which have a support which has a macropore fraction of less than 5%. Such catalysts are described, for example, in DE 102 25 565 and DE 102 32 868, to which reference is made explicitly and whose contents are incorporated in the subject matter of the present description.

The catalysts used for the hydrogenation may also be the catalysts described in WO 2004/046078, to which reference is made explicitly and whose contents are incorporated in the subject matter of the present description. These catalysts have a hydrogenation-active metal, preferably a transition metal of group VIII, especially selected from the group comprising platinum, rhodium, palladium, cobalt, nickel or ruthenium, or from transition group I or VII of the periodic table of the elements, on a support material which comprises a material having ordered mesopores. The material used which has ordered mesopores may, for example, be silica.

In addition, all catalysts used in the process according to the invention may additionally comprise an inert component (support) which contains at least one metal from the group of Al, Mg, Ti, Zr and/or Si, as an oxide or mixed oxide. Optionally, the catalysts may also comprise salts of the abovementioned metals, for example sulfates and/or phosphates. In addition, the catalysts used in accordance with the invention may also include processing and shaping assistants, for example graphite.

Preferred compositions are specified hereinbelow. The compositions each relate to the reduced catalysts.

The content in the catalysts of the metals of transition group VIII mentioned (calculated as the metal) is preferably in the range from 1 to 60% by mass, in particular in the range from 25 to 45% by mass, most preferably in the range of from 30 to 40% by mass.

The content in the catalysts of metals of transition group II, III, IV, V and/or VI (calculated as the oxide) is from 10 to 90% by mass, in particular from 20 to 60% by mass, very particularly from 20 to 40% by mass.

In the hydrogenation, particular preference is given to using catalysts which contain, in reduced, active form, nickel, at least partly in the 0 oxidation state, and zinc, preferably in the +2 oxidation state.

The catalysts are prepared by processes known per se. Preference is given to preparing the catalysts by precipitation of soluble metal salts. In order to prepare a catalyst which comprises, for example, the main components of nickel, zinc oxide and silicon dioxide as a support, it is possible, for example, to precipitate nickel carbonate and zinc carbonate in a suspension of silica and optionally graphite in water. Further steps known to those skilled in the art for preparing the catalyst are: removal and washing of the precipitate, drying, calcination, shaping and reduction.

The catalysts are appropriately brought into a shape which offers low flow resistance in the hydrogenation, for example tablets, cylinders, extrudates or rings.

In this embodiment of the process according to the invention, it is possible, in the hydrogenation step, for example, to use the commercially available catalyst H10126 from Degussa AG, Dusseldorf. This catalyst has been used to date only for the hydrogenation of aromatic and olefinic hydrocarbons in halogen- and sulfur-containing raw materials. Its use for the ring hydrogenation of aromatic esters has only rarely been described. This catalyst contains 32% by mass of nickel, 29% by mass of zinc oxide, 24% by mass of silicon dioxide.

In addition to nickel-containing catalysts, it is also possible in particular to use catalysts which have ruthenium as the active metal. In addition to ruthenium, additionally at least one metal of the first and/or seventh transition group of the periodic table of the elements may be present as the active metal in the catalysts. The further active metal used is preferably rhenium and/or copper.

The ruthenium-containing catalysts used are preferably supported catalysts. The supports used may, for example, be the following substances: activated carbon, silicon carbide, aluminum oxide, silicon oxide, aluminosilicate, titanium dioxide, zirconium dioxide, magnesium oxide and/or zinc oxide or mixtures thereof. Particular preference is given to using a catalyst which has a titanium dioxide support. In addition, these support materials may comprise alkali metals, alkaline earth metals and/or sulfur.

The content of the active metals, i.e. of the metals of the first and/or seventh and/or eighth transition group of the periodic table of the elements in the catalyst is generally from 0.1 to 30% by mass. The ruthenium content, calculated as the metal, is preferably in the range from 0.1 to 10% by mass, in particular in the range from 0.8 to 5% by mass, very particularly in the range between 1 and 3% by mass.

The preparation of such ruthenium-containing catalysts can be taken from the documents DE 102 25 565 and DE 102 32 868, to which reference is made explicitly and whose contents are incorporated in the disclosure content of the present description.

In this embodiment of the process according to the invention, the hydrogenation is preferably carried out in the liquid phase. The hydrogenation may be carried out continuously or batchwise over suspended or particulate catalysts arranged in a fixed bed. In the process according to the invention, preference is given to a continuous hydrogenation over a catalyst arranged in a fixed bed, in which the product/reactant phase is present mainly in the liquid state under reaction conditions.

When the hydrogenation is carried out continuously over a catalyst arranged in a fixed bed, it is appropriate to convert the catalyst to the active form before the hydrogenation. This can be done by reduction of the catalyst with hydrogen-containing gases by a temperature program. The reduction can be carried out, if appropriate, in the presence of a liquid phase which trickles over the catalyst. The liquid phase used may be a solvent or the hydrogenation product.

For the hydrogenation, different process variants may be selected. It may be carried out in one or more stages adiabatically, polytropically or virtually isothermally, i.e. with a temperature rise of typically less than 10° C. In the latter case, it is possible to operate all reactors, appropriately tubular reactors, adiabatically or virtually isothermally, and also to operate one or more adiabatically and the others virtually isothermally. It is also possible to hydrogenate the aromatic polycarboxylic esters in straight pass or with product recycling.

The hydrogenation may be carried out in the liquid/gas mixed phase or in the liquid phase in three-phase reactors in cocurrent, in which case the hydrogenation gas is distributed in the liquid reactant/product stream in a manner known per se. In the interests of uniform liquid distribution, of improved removal of heat of reaction and a high space-time yield, the reactors are preferably operated with high superficial velocities of from 15 to 120 m³, in particular from 20 to 80 m³, per m² of cross section of the empty reactor and hour. When a reactor is operated in straight pass, the specific catalyst hourly space velocity (LHSV) can assume values between 0.1 and 10 h⁻¹.

The hydrogenation may be carried out in the absence or preferably in the presence of a solvent. The solvents used may be all liquids which form a homogeneous solution with the reactant and product, behave inertly under hydrogenation conditions and can be removed readily from the product. The solvent may also be a mixture of a plurality of substances and optionally comprise water.

For example, the solvent used may be the following substances:

straight-chain or cyclic ethers, for example tetrahydrofuran or dioxane, and also aliphatic alcohols in which the alkyl radical has from 1 to 13 carbon atoms. Alcohols usable with preference are, for example, isopropanol, n-butanol, isobutanol, n-pentanol, 2-ethylhexanol, nonanols, technical nonanol mixtures, decanol, technical decanol mixtures, tridecanols.

When alcohols are used as the solvent, it may be appropriate to use that alcohol or that alcohol mixture which would form in the hydrolysis of the product, i.e. here the mixture of isomeric nonanols. This rules out by-product formation as a result of transesterification. A further preferred solvent is the hydrogenation product itself.

The use of a solvent can restrict the aromatics concentration in the reactor feed, which can result in better temperature control in the reactor being achieved. This can have the consequence of minimization of side reactions and thus an increase in the product yield. The aromatics content in the reactor feed is preferably between 1 and 35%, in particular between 5 and 25%. The desired concentration range may, in reactors which are operated in loop mode, be adjusted by virtue of the circulation rate (quantitative ratio of recycled hydrogenation effluent to reactant).

The hydrogenation may be carried out in a pressure range from 3 to 25 MPa, in particular from 5 to 10 MPa. The hydrogenation temperatures are preferably in the range from 60 to 200° C., in particular in the range from 80 to 140° C.

The hydrogenation gases used may be any hydrogen-containing gas mixtures which do not contain harmful amounts of catalyst poisons, for example carbon monoxide or hydrogen sulfide. The inert gas constituents may, for example, be nitrogen or methane. Preference is given to using hydrogen in a purity of greater than 95%, in particular greater than 98%.

In a second embodiment of the process according to the invention, the mixture of DINCH is obtained by transesterifying esters of 1,2-cyclohexanedicarboxylic acid with a mixture of isomeric nonanols which has a degree of branching of from 1.2 to 2.0, preferably a degree of branching of from 1.2 to 1.9, preferentially from 1.3 to 1.8 and more preferably from 1.3 to 1.7. Preference is given to reacting alkyl esters of 1,2-cyclohexanedicarboxylic acid whose alkyl radicals have from 1 to 9, preferably from 2 to 8 carbon atoms, with the mixture of isomeric nonanols in a transesterification. These allkyl radicals may be aliphatic, straight-chain or branched, alicyclic or aromatic. One or more methylene groups of these alkyl radicals may be substituted by oxygen. It is appropriate that the parent alcohols of the reactant ester have a lower boiling point than the mixture of isomeric nonanols used, preferably lower than the lowest-boiling nonanol which is present in the mixture of the isomeric nonanols. In the process according to the invention, preference is given to transesterifying one or more alkyl esters of 1,2-cyclohexanedicarboxylic acid, selected from the dimethyl esters, diethyl esters, dipropyl esters, diisobutyl esters, diamyl esters and/or dibutyl esters. A very particularly preferred feedstock is the dimethyl ester of 1,2-cyclohexanedicarboxylic acid.

Esterification is preferably carried out catalytically, for example with Brønsted or Lewis acids or bases. Quite irrespective of which catalyst is used, a temperature-dependent equilibrium always forms between the feedstocks (alkyl esters and mixture of isomeric nonanols) and the products (mixture of isomeric diisononyl cyclohexanedicarboxylates and released alcohols). In order to shift the equilibrium in favor of the nonyl ester or of the isononyl ester mixture, the alcohol formed from the reactant ester is preferably distilled out of the reaction mixture. It is appropriate to use the mixture of isomeric nonanols in excess. Preference is given to using from 5 to 50%, in particular from 10 to 30% more mixture of isomeric nonanols than corresponds to the amount needed to form the ester.

The transesterification catalysts used may be acids, for example sulfuric acid, methanesulfonic acid or p-toluenesulfonic acid, or metals or their compounds. Suitable examples are tin, titanium, zirconium, which may be used in the form of finely divided metals or appropriately in the form of their salts, oxides or as soluble organic compounds. In contrast to protic acids, the metal catalysts are high-temperature catalysts which attain their full activity only at temperatures above 180° C. However, they are used with preference because they form fewer by-products, for example olefins from the alcohol used, in comparison to protic catalysis. Examples of representatives of metal catalysts are tin powder, tin(II) oxide, tin(II) oxalate, titanic esters such as tetraisopropyl orthotitanate or tetrabutyl orthotitanate, and also zirconium esters such as tetrabutyl zirconate.

It is also possible to use basic catalysts, for example oxides, hydroxides, hydrogencarbonates, carbonates or alkoxides of alkali metals or alkaline earth metals. Among this group, preference is given to using alkoxides, for example sodium methoxide. Alkoxides may also be prepared in situ from an alkali metal and a nonanol or an isononanol mixture. The catalyst concentration depends upon the type of the catalyst. It is typically between 0.005 and 1.0% by mass based on the reaction mixture.

The reaction temperatures for the transesterification are typically in the range from 100 to 220° C. They have to be at least sufficiently high that the alcohol formed from the reactant ester can be distilled out of the reaction mixture at the given pressure, usually standard pressure.

The transesterification mixtures may be worked up exactly as has been described for the esterification mixtures from the esterification step of the first embodiment of the process according to the invention.

In a third embodiment of the process according to the invention, the mixture of DINCH is obtained by esterifying 1,2-cyclohexanedicarboxylic acid or a corresponding derivative, especially the corresponding anhydride, with the mixture of isomeric nonanols which has a degree of branching of from 1.2 to 2.0, preferably a degree of branching of from 1.2 to 1.9, preferably from 1.3 to 1.8 and more preferably from 1.3 to 1.7. The esterification can be effected in the same way as described in the esterification step of the first embodiment of the process according to the invention, with the difference that 1,2-cyclohexanedicarboxylic acid is used instead of phthalic acid or the anhydride of 1,2-cyclohexanedicarboxylic acid is used instead of phthalic anhydride. 1,2-Cyclohexanedicarboxylic acid or its anhydride are obtainable, for example, from Aldrich.

In a further embodiment of the process according to the invention for preparing DINCH, a dicarboxylic acid or the corresponding derivative, especially the corresponding anhydride, is esterified with the mixture of isomeric nonanols which has a degree of branching of from 1.2 to 2.0, preferably a degree of branching of from 1.2 to 1.9, preferably from 1.3 to 1.8 and more preferably from 1.3 to 1.7, the dicarboxylic acid or the corresponding derivative, especially the anhydride, being obtained by a process which includes a Diels-Alder reaction step. This process may include, for example, the following steps:

1. conversion of a butadiene-maleic anhydride mixture to cyclohexenedicarboxylic anhydride in condensed phase,
2. ester formation from the cyclohexenedicarboxylic anhydride by esterification with a mixture of isomeric nonanols which has a degree of branching of from 1.2 to 2.0, preferably a degree of branching of from 1.2 to 1.9, preferentially from 1.3 to 1.8 and more preferably from 1.3 to 1.7, and
3. hydrogenation of the cyclohexene derivative from step (2) to give the corresponding cyclohexanedicarboxylic ester or 1. conversion of a butadiene-maleic anhydride mixture to cyclohexenedicarboxylic anhydride in condensed phase,
2. hydrogenation of the cyclohexenedicarboxylic anhydride to cyclohexanedicarboxylic anhydride and
3. ester formation from the cyclohexanedicarboxylic anhydride by esterification with a mixture of isomeric nonanols which has a degree of branching of from 1.2 to 2.0, preferably a degree of branching of from 1.2 to 1.9, preferentially from 1.3 to 1.8 and more preferably from 1.3 to 1.7.

What is crucial in this process is the use of mixtures of isomeric nonanols which have a suitable degree of branching. The remaining process parameters can be taken from DE 101 61 010, whose disclosure is referred to explicitly and is incorporated in the disclosure content of the present invention.

The inventive mixtures may also be obtained by mixing diisononyl esters of 1,2-cyclohexanedicarboxylic acid or mixtures thereof which have different degrees of branching with regard to the isononyl radicals, and which in particular, each taken alone, have a degree of branching outside the claimed range. The mixing can be undertaken by customary processes.

The inventive mixtures of diisononyl esters of 1,2-cyclohexanedicarboxylic acid may be used in paints, inks or coatings, in plastisols, adhesives or adhesive components, in sealants or as plasticizers in plastics or plastic components or as solvents. Preferred plastisols are in particular PVC plastisols. Preferred plastics are PVC, homo- and copolymers based on ethylene, propylene, butadiene, vinyl acetate, glycidyl acrylate, glycidyl methacrylate, methacrylates, acrylates, acrylates with alkyl radicals, bonded on the oxygen atom of the ester group, of branched or unbranched alcohols having from 1 to 10 carbon atom(s), styrene, acrylonitrile, homo- or copolymers of cyclic olefins.

Examples of representatives of the above groups include, for example, the following polymers:

polyacrylates with identical or different alkyl radicals having from 4 to 8 carbon atoms, bonded to the oxygen atom of the ester group, especially with the n-butyl, n-hexyl, n-octyl and 2-ethylhexyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers, PVB and PVC.

It is also possible to use the inventive mixtures for modifying polymer mixtures, for example the mixture of a polyolefin with a polyamide.

Mixtures of polymers, especially PVC, which comprise the inventive mixtures of diisononyl esters of 1,2-cyclohexanedicarboxylic acid may be present, for example, in the following products:

casings for electrical appliances, for example kitchen appliances, computer casings, casings and components of phonographic units and television sets, pipelines, equipment, cables, wire sheathing, insulation tapes, in interior fittings, in vehicle and furniture construction, plastisols, in floorcoverings, medical items, food packaging, seals, films, composite films, phonographic disks, synthetic leather, toys, packaging containers, adhesive tape films, clothing, coatings, fibers for fabrics, coated fabrics.

It is also possible to use mixtures of polymer, especially PVC, which comprise inventive mixtures of diisononyl esters of 1,2-cyclohexanedicarboxylic acid, for example, to produce the following items:

casings for electrical appliances, pipelines, hoses, cables, wire sheathing, insulation tapes, in vehicle and furniture construction, plastisols, window profiles, floorcoverings, medical items (for example blood bags), toys, food packaging, seals, films, composite films, disks, phonographic disks, synthetic leather, wallpaper, packaging containers, adhesive tape films, clothing, coatings or fibers for fabric, shoes, underseal, seam sealants, modeling materials or balls.

Such mixtures of polymer, especially plasticized PVC or plastisols which comprise PVC and inventive mixtures of diisononyl esters of 1,2-cyclohexanedicarboxylic acid contain preferably from 5 to 120 parts by mass, preferably from 10 to 100 parts by mass and more preferably from 20 to 80 parts by mass of the inventive mixtures of diisononyl esters of 1,2-cyclohexanedicarboxylic acid per 100 parts by mass of PVC.

In addition to the abovementioned applications, the inventive mixtures of diisononyl esters of 1,2-cyclohexanedicarboxylic acid may be used as a lubricant oil component, as a constituent of cooling fluids and metalworking fluids.

The examples which follow will illustrate the invention without restricting the scope of protection defined by the claims.

EXAMPLES

Example 1

Preparation of 3,5,5-trimethylhexanol

In a 2 l autoclave, 1000 g of 2,4,4-trimethyl-1-pentene (diisobutene, manufacturer: OXENO Olefinchemie GmbH) were hydroformylated at 135° C. under 270 bar of synthesis gas pressure for 3 hours in the presence of an unmodified rhodium catalyst. The active catalyst was generated in situ from rhodium nonanoate (with 24.8% by weight of Rh). The rhodium concentration based on diisobutene was adjusted to 20 ppm. After 3 hours, the reaction was stopped and the autoclave cooled to 20° C. The reaction effluent contained 93.5% by weight of 3,5,5-trimethylhexanal, 2.5% by weight of 3,5,5-trimethylhexanol, 3.4% by weight of $C_8$ residual hydrocarbons and 0.6% by weight of high boilers (determined by GC). In a laboratory distillation column, the reaction effluent was freed of rhodium catalyst by distillation.

The Rh-free hydroformylation effluent was subsequently hydrogenated at 180° C. and 25 bar in the liquid phase in a fixed bed reactor in the presence of a Cu/Cr/Ni catalyst (H14279; Degussa AG, Dusseldorf). After the hydrogenation of 3,5,5-trimethylhexanal to the 3,5,5-trimethylhexanol target product, the hydrogenation effluent was freed of the low boilers ($C_8$ hydrocarbons) by controlled distillation. After the distillation, 3,5,5-trimethylhexanol with a purity of over 99.5% was obtained.

Example 2

Preparation of Various Diisononyl Cyclohexane-1,2-dicarboxylates (DINCH)

The $C_9$ alcohols listed in table 1, commercially available apart from A, were converted to the corresponding cyclohexane-1,2-dicarboxylic esters by the following method:

A 2 l distillation flask was initially charged with 462 g (3 mol) of cis-hexahydrophthalic anhydride (Fluka), 1296 g of nonyl alcohol (9 mol) corresponding to table 1, 200 ml of toluene and 1.94 g of tetraisononyl titanate, and esterified under standard pressure with a reflux at 180° C. for 7.5 hours. The temperature was kept constant over the addition of toluene. After 7.5 hours, the acid number was ≦0.1 mg KOH/g (here and in the examples adduced below, determined according to DIN EN ISO 2114, by the calorimetric titration process according to process A, the solvent used having been a toluene/isopropanol/water mixture with a volume ratio of 1 to 1.5 to 0.2), which corresponds to an over 99.9% conversion of the cyclohexanoic anhydride.

Thereafter, first the toluene at up to 120° C. at 50 hPa and then the alcohol excess at up to 180° C. at 5 hPa were distilled off via a Claisen head with condenser. A further acid number determination determined the amount of sodium hydroxide solution required for the neutralization. Subsequently, the mixture was neutralized with sodium hydroxide solution in a 2 l reaction flask at 80° C. under standard pressure by stirring for 30 minutes.

After the neutralization, the apparatus was evacuated and heated to 180° C. An immersed tube with attached dropping funnel was used to slowly add water dropwise at 180° C. and 5-20 hPa in order to purify the ester. On completion of purification, the heating was switched off and the product was cooled under reduced pressure. At 100° C., the ester was filtered through a suction filter with filter paper (type 389, Filtrak) and filter assistant (Perlite).

TABLE 1

| Designation | Origin/trade name |
| --- | --- |
| A | 3,5,5-Trimethylhexanol according to example 1 (comparative example) |
| B | EXXAL 9 (Exxon-Mobil) |
| C | EXXAL 9-S (Exxon-Mobil) |

TABLE 1-continued

| Designation | Origin/trade name |
| --- | --- |
| D | Isononanol (OXENO) |
| E | Nonanol N (BASF) |

Example 3

NMR Spectroscopy Analysis of the Different DINCH Types

| | |
| --- | --- |
| Analytical instrument: | Avance 500 NMR spectrometer from Bruker |
| Analysis frequency: | 500 MHz |
| Probehead: | BBO probehead, 5 mm |
| Solvent: | $CDCl_3$ (99.8% deuteration) |
| Standard: | Tetramethylsilane (TMS) |
| Analysis temperature: | 300 K |
| Number of scans: | 32 |
| Delay: | 5 s |
| Acquisition time: | 3.3 s |
| Spectral width: | 10 000 Hz |
| Pulse angle: | 30° |
| Pulse length (90°): | 9.7 µs |

To record the $^1$H NMR spectra, approx. 20 mg of the sample were dissolved in approx. 0.6 ml of $CDCl_3$ (with 1% by weight of TMS) and transferred to an NMR tube with a diameter of 5 mm. The spectra were recorded under the above-specified conditions and referenced to TMS=0 ppm. The area under the signals in the range from 0.5 ppm up to the minimum of the lowest valley in the range from 0.9 to 1.1 ppm was integrated. The area in this region is determined substantially by the signals of the hydrogen atoms which belong to a methyl group. The area under the signals in the range from 3.6 ppm to 4.4 ppm was likewise integrated. The area in this region is determined substantially by the signals of the methylene hydrogen atoms of the methylene group which is adjacent to the oxygen of the alcohol or of the alcohol radical. The integration was effected with the software xwinnmr 3.5 (from Bruker). The degree of branching can then be determined from the ratio of the area integral which is attributed substantially to the methyl hydrogen atoms $I(CH_3)$, divided by three (for the three methyl hydrogen atoms), to the area integral of the methylene hydrogen atoms adjacent to the oxygen $I(OCH_2)$, divided by 2 (for the two methylene hydrogen atoms), minus one according to the following formula:

$$V = \frac{2}{3} * I(CH_3)/I(OCH_2) - 1$$

The degrees of branching of the DINCH types A to E are listed in table 2, column 3.

Example 4

Determination of the Glass Transition Temperature ($T_G$)

By means of DSC analysis to DIN 51 007 (June 1994 edition), the glass transition temperatures of the plasticizers prepared according to example 2 and of DEHP were then determined. To this end, from 10 to 15 mg of sample were analyzed in a tightly sealed aluminum crucible (40 µl) with a DSC820 instrument from Mettler. The heating rates from −150° C. to +50° C. were 5 K/min. The sample was cooled to start temperature in an uncontrolled manner (as fast as possible). Since the crucible was sealed tightly, it was possible to work with ambient atmosphere without any special atmosphere or any special gas flow. The calibration was effected with indium. The evaluation was effected with the software STARe 8.10. The results are listed in table 2 which follows.

TABLE 2

| Designation | Alcohol used | Degree of branching according to example 3 | Glass transition temperature $T_G$ in °C. according to example 4 |
|---|---|---|---|
| DINCH-A | 3,5,5-Trimethylhexanol (according to example 1, comparative example) | 3.1 | −69.7 |
| DINCH-B | EXXAL 9 (ExxonMobil) | 1.91 | −83.2 |
| DINCH-C | EXXAL 9-S (ExxonMobil) | 1.72 | −85.4 |
| DINCH-D | Isononanol (OXENO) | 1.31 | −90.4 |
| DINCH-E | Nonanol N (BASF) | 1.24 | −91.0 |

For DEHP, a glass transition temperature $T_G$ of −85.5° C. is obtained by this method. Owing to the somewhat lower plasticizing action of DINCH and compared to DEHP, and to a higher dosage of DINCH that this might necessitate, it can be assumed, however, that DINCH-B, whose $T_G$ differs only slightly from that of DEHP, would also be suitable in principle.

In these examples, there is a clear correlation between degree of branching and glass transition temperature. With the "KORREL" function from MS Excel, it is possible here to obtain a correlation coefficient of >0.99.

It is thus found that, in the case of degrees of branching above 2, the necessary cold flexibility can no longer be achieved, which is needed, for example, in the case of storage of medical products in containers made of plastized PVC.

Example 5

Production of Plastized PVC Specimens 600 g of suspension PVC of Solvic 271 PC type were mixed with 400 g of plasticizer according to table 2 and also 24 g of the stabilizer BP MC 8823 (from Baerlocher) with a hand mixer at room temperature. The mixture was subsequently plasticized on a steam-heatable laboratory roll mill (from Collin, type 150) and processed to a rolled sheet. In the case of the cyclohexanedicarboxylic esters, the temperature of the two rollers was 170° C. in each case, and 165° C. when the plasticizer DEHP was used. The rolling time was 5 minutes. The cooled rolled sheet was then pressed in a hydraulic hand press (60 t) from Werner & Pfleiderer as follows: the temperature was adjusted to 175° C. (to 170° C. in the case of DEHP-containing rolled sheet) and the sheet was pressed first at 50 bar for 2 minutes, then at 100 bar for 1 minute and finally once more at 180 bar for 2 minutes. The pressure was then increased to 200 bar and the sheet was cooled to room temperature at this pressure.

Example 6

Determination of the Glass Transition Temperature of the Specimens

From the specimens produced according to example 5, 60 mm-long, 8 mm-wide and 1 mm-thick pieces were punched out and the stiffness G' and the loss modulus G" of these were each determined in a MYRENNE ATM III torsion pendulum according to DIN EN ISO 6721 (part 2, process B, clamped length 50 mm) at temperatures of from −100° C. to +100° C. and a frequency of 1 s$^{-1}$. It was possible to determine the glass transition temperature $T_G$ from the maximum of G". This is a measure of the flexibility at low temperatures. The glass transition temperatures of the specimens are listed in table 3.

Example 7

Determination of the Loss of Mass of the Specimens After Thermal Aging

Seven days after the production of the 1 mm-thick rolled sheets according to example 5, tensile specimens according to ISO 527 type 5 were punched out and pierced on the short side. Thereafter, the test specimens were stored under standard climatic conditions, (23° C., 50% relative atmospheric moisture) for at least 24 h. From each series, three test specimens were weighed to 0.1 g precisely on an analytical balance and then stored hanging in a Heraeus (now Kendro) UT 6060 drying cabinet at 100° C. with fresh air supply (approx. 2.6 m$^3$ per hour) for 7 days. The temperature was measured by means of a PT100 temperature sensor independent of the unit (mounted in the interior, distance from wall min. 100 mm). To maintain a sufficient distance between the samples (5 mm), Raschig rings were used. A minimum distance of 30 mm from the interior walls was maintained.

After the aging, the samples were taken from the drying cabinet and again treated under standard climatic conditions (23° C., 50% relative atmospheric moisture) for at least 24 h and subsequently weighed again. The percentage loss of mass is calculated from the difference of the weights based on the starting mass. The loss of mass is listed in table 3.

TABLE 3

| Plasticizer used | $T_G$ in °C. according to example 7 | Loss of mass after thermal aging (7 d/100° C.) according to example 8 |
|---|---|---|
| DINCH-A | −27° C. | 19% |
| DINCH-D | −44° C. | 3% |
| DEHP | −35° C. | 6% |

The results from table 3 clearly show a dependence of the performance properties upon the structure and the degree of branching of the DINCH used. It can be seen clearly that, with a DINCH based on 3,5,5-trimethylhexanol, distinctly poorer properties are achieved than with a DINCH which is based on an alcohol which has a degree of branching within the claimed range.

What is claimed is:

1. A mixture of diisononyl esters of 1,2-cyclohexanedicarboxylic acid, wherein the isononyl radicals of the diisononyl esters present in the mixture have a degree of branching of from 1.2 to 2.0.

2. The mixture as claimed in claim 1, wherein nonyl alcohols obtained by hydrolysis of the diisononyl esters contain less than 10 mol % of 3,5,5-trimethylhexanol.

3. The mixture as claimed in claim 1, wherein the isononyl radicals of the diisononyl esters present in the mixture have a degree of branching of from 1.2 to 1.9.

4. The mixture as claimed in claim 3, wherein the isononyl radicals of the diisononyl esters present in the mixture have a degree of branching of from 1.3 to 1.8.

5. The mixture as claimed in claim 1, wherein the diisononyl esters present in the mixture have a degree of branching of from 1.3 to 1.7.

6. The mixture as claimed in claim 1, wherein the isononyl radicals of the diisononyl esters present in the mixture have a degree of branching of from 1.24 to 1.91 and contain less than 10 mol % of 3,5,5-trimethylhexyl radicals, and wherein the mixture has a glass transition temperature $T_G$ of from −91.0 to −83.2° C.

7. A process for preparing mixtures of diisononyl esters of 1,2-cyclohexanedicarboxylic acid from a mixture of isomeric nonanols which has a degree of branching of from 1.2 to 2.0 in the preparation of the diisononyl esters comprising reacting the mixture of isomeric nonanols with phthalic acid or phthalic anhydride in an esterification step to give diisononyl phthalates and subsequently ring-hydrogenating said diisononyl phthalates.

8. The process as claimed in claim 7, wherein mixtures of isomeric nonanols which contain less than 10 mol % of 3,5,5-trimethylhexanol are used.

9. The process as claimed in claim 7, wherein the hydrogenation of the diisononyl phthalates is carried out over a catalyst which comprises at least one metal from transition group VIII, optionally together with at least one metal of transition group II, III, IV, V and/or VI of the periodic table.

10. The process as claimed in claim 7, wherein alkyl esters of 1,2-cyclohexanedicarboxylic acid whose alkyl radicals have from 1 to 9 carbon atoms are reacted with the mixture of isomeric nonanols in a transesterification.

11. The process as claimed in claim 7, wherein 1,2-cyclohexanedicarboxylic acid or a corresponding acid derivative is esterified with the mixture of isomeric nonanols.

12. The process as claimed in claim 7, wherein a dicarboxylic acid or a corresponding acid derivative which is obtained by a process which includes a Diels-Alder reaction step is reacted with the mixture of isomeric nonanols.

13. The process as claimed in claim 7, wherein the mixture of isomeric nonanols used is a mixture which is obtainable by hydroformylation and subsequent or simultaneous hydrogenation of a mixture of isomeric octenes, the mixture of isomeric octenes being obtained by contacting a hydrocarbon mixture which comprises butenes and has a content of isobutene of less than 20% by weight based on the butenes present with a catalyst comprising nickel oxide.

14. The process as claimed in claim 13, wherein the hydrocarbon mixture comprising butenes has a content of isobutene between 0.01 and 1% by weight based on the butenes present.

15. The process as claimed in claim 7, wherein the mixture of isomeric nonanols is a mixture which is obtainable by oligomerization of olefins over a solid acidic catalyst.

16. The process as claimed in claim 7, wherein the mixture of isomeric nonanols is a mixture which is obtained by mixing isomerically pure nonanols and/or fractions of a plurality of isomeric nonanols.

17. A process for preparing a mixture as claimed in claim 1, comprising:
obtaining the mixture of diisononyl esters of 1,2 cyclohexanedicarboxylic acid by mixing mixtures of diisononyl esters of 1,2-cyclohexanedicarboxylic acid which have different degrees of branching with regard to the isononyl radicals.

18. A process of obtaining a mixture comprising mixing the mixture as claimed in claim 1 with paints, inks or coatings, plastisols, adhesives or adhesive components, sealants, plasticizers in plastics or plastic components, solvents, lubricant oil components and assistants in metal processing.

19. The process as claimed in claim 18, wherein the plastic is PVC.

20. The process as claimed in claim 18, wherein the plastisol is a PVC plastisol.

21. A plasticized PVC comprising PVC and from 5 to 120 parts by mass of a mixture as claimed in claim 1 per 100 parts by mass of PVC.

22. A plastisol comprising PVC and from 5 to 120 parts by mass of a mixture as claimed in claim 1 per 100 parts by mass of PVC.

23. A plasticized PVC comprising PVC and from 5 to 120 parts by mass of a mixture as claimed in claim 6 per 100 parts by mass of PVC.

24. A plastisol comprising PVC and from 5 to 120 parts by mass of a mixture as claimed in claim 6 per 100 parts by mass of PVC.

\* \* \* \* \*